United States Patent
Hsieh et al.

(10) Patent No.: US 10,006,864 B2
(45) Date of Patent: Jun. 26, 2018

(54) CARRIER CONCENTRATION MEASURING METHOD AND APPARATUS THEREOF

(71) Applicant: INDUSTRIAL TECHNOLOGY RESEARCH INSTITUTE, Hsinchu (TW)

(72) Inventors: Cho-Fan Hsieh, Luodong Township, Yilan County (TW); Chih-Hua Chen, Taipei (TW); Ming-Han Liao, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 148 days.

(21) Appl. No.: 14/968,379

(22) Filed: Dec. 14, 2015

(65) Prior Publication Data

US 2017/0097303 A1    Apr. 6, 2017

(30) Foreign Application Priority Data

Oct. 5, 2015  (TW) .............................. 104132673 A

(51) Int. Cl.
  *G01N 21/65* (2006.01)
  *G01J 3/44* (2006.01)
(52) U.S. Cl.
  CPC ............... *G01N 21/65* (2013.01); *G01J 3/44* (2013.01)
(58) Field of Classification Search
  CPC ..................................................... G01N 21/65
  (Continued)

(56) References Cited

U.S. PATENT DOCUMENTS 5,417,494 A * 5/1995 Kempa ................... G01N 25/72
                                                    219/711
6,151,119 A   11/2000 Campion et al.
(Continued)

FOREIGN PATENT DOCUMENTS

CN     10263997 A     8/2012
CN    104597034 A     5/2015
(Continued)

OTHER PUBLICATIONS

Takashi Sasaki, Shintaro Nishibe, Hiroaki Minami, Kenji Kisoda, Toshiyuki Isshiki, Masahiro Yoshimoto, Woo Sik Yoo, and Hiroshi Harima, "Deep-UV Raman Scattering Analysis of Re-Crystallization in Ultra-Shallow Junction Implanted Si Under Various Annealing Conditions", Kyoto Institute of Technology, Japan, Wakayama University, Japan, Wafermasters, Inc, California, U.S.A. p. 1-4, Jun. 2007.
(Continued)

*Primary Examiner* — Tarifur Chowdhury
*Assistant Examiner* — Omar Nixon
(74) *Attorney, Agent, or Firm* — Muncy, Geissler, Olds & Lowe, P.C.

(57) ABSTRACT

A carrier concentration measuring method and an apparatus thereof including a focuser, a spectrometer and a processor are disclosed. The measuring method includes the following steps. Project a laser beam to an object. Analyze a Raman signal, obtained from a radiation propagating from the object projected by the laser beam, to obtain a measurement result of the object. Analyze the measurement result to obtain an intensity ratio or a Raman shift. Look up a carrier concentration of the object in a database according to the intensity ratio or the Raman shift.

10 Claims, 8 Drawing Sheets

(58) Field of Classification Search
USPC .................................................... 356/301
See application file for complete search history.

(56) References Cited

U.S. PATENT DOCUMENTS

| | | | |
|---|---|---|---|
| 6,867,858 B2 | 3/2005 | Owen et al. | |
| 7,610,080 B1* | 10/2009 | Winchester, Jr. | .... A61B 5/0059 |
| | | | 600/407 |
| 2008/0129992 A1* | 6/2008 | Matousek | ............ A61B 5/0059 |
| | | | 356/301 |
| 2012/0062884 A1* | 3/2012 | Sakagami | ............. G01J 3/0224 |
| | | | 356/301 |
| 2012/0215078 A1* | 8/2012 | Kawamura | ........ A61B 5/14532 |
| | | | 600/316 |
| 2012/0274934 A1* | 11/2012 | Messerschmidt | ...... G01N 21/65 |
| | | | 356/301 |
| 2013/0131488 A1* | 5/2013 | Zeng | .................... A61B 5/0071 |
| | | | 600/408 |
| 2014/0239181 A1* | 8/2014 | Hattori | ............... G01B 11/0625 |
| | | | 250/339.08 |
| 2014/0370627 A1 | 12/2014 | Li | |
| 2015/0008327 A1 | 1/2015 | Caneau et al. | |

FOREIGN PATENT DOCUMENTS

| | | |
|---|---|---|
| TW | I272730 | 10/2003 |
| TW | I420094 | 4/2007 |

OTHER PUBLICATIONS

Woo Sik Yoo, Kitaek Kang, Takeshi Ueda, and Toshikazu Ishigaki, "Design of Multi-Wavelength Micro Ramen Spectroscopy System and Its Semiconductor Stress Depth Profiling Applications", The Japan Society of Applied Physic, 2009, Wafermasters, Inc. CA 95112, U.S.A., Published Online Nov. 6, 2009, p. 1-3.

Jing-Chung Huang, "Properties of Nitrogen Implanted GaN" National Central University, Department of Optics and photonics Master's thesis, Jul. 2000, Spec. p. 37-38, Fig 4. 11-4. 15 (Specification Abstract, col. 2 Lines 1-20, col. 4 Line 34, col. 10 Line 58, Fig 2,6,8).

* cited by examiner

CARRIER CONCENTRATION MEASURING METHOD AND APPARATUS THEREOF

CROSS-REFERENCE TO RELATED APPLICATIONS

This non-provisional application claims priority under 35 U.S.C. § 119(a) on Patent Application No(s). 104132673 filed in Taiwan, R.O.C. on Oct. 5, 2015, the entire contents of which are hereby incorporated by reference.

TECHNICAL FIELD

The disclosure relates to a carrier concentration measuring method and an apparatus thereof.

BACKGROUND

Minimizing semiconductor components leads to the limitation in the depth of the junction that carriers can be implanted into the semiconductor components so that the design of the carrier concentration distribution of the junction within the semiconductor components have become more important. The concentration of doped carriers within the junction of the semiconductor components is affected by fabrication processes and material properties, such as the type of doped carriers, the temperature setting in the fabrication process, being annealed or not being annealed, or any defect within the semiconductor components during the manufacture.

A present method to measure the concentration distribution of doped carriers is to use a secondary ion mass spectrometer (SIMS) to destructively analyze semiconductor components. However, such a destructive measurement method is adapted to measure only a couple samples among all objects to be measured and will damage these samples. Therefore, this method and secondary ion mass spectrometers cannot be applied to production lines.

SUMMARY

According to one or more embodiments, the disclosure provides a carrier concentration measuring method including the following steps. Project a laser beam to an object, and analyze a Raman signal, obtained from a radiation propagating from the object projected by the laser beam, to obtain a, measurement result of the object. Analyze the measurement result to obtain an intensity ratio or a. Raman shift. Look up a carrier concentration of the object in a database according to the intensity ratio or the Raman shift.

According to one or more embodiments, the disclosure provides a carrier concentration measuring apparatus including a focuser, a spectrometer, and a processor. The focuser projects a laser beam to an object and receives a radiation, propagating from the object projected by the laser beam, to obtain a Raman signal. The spectrometer analyzes the Raman signal to obtain a measurement result of the object. The processor analyzes the measurement result to obtain an intensity ratio or a Raman shift and looks up a carrier concentration of the object in a database according to the intensity ratio or the Raman shift.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
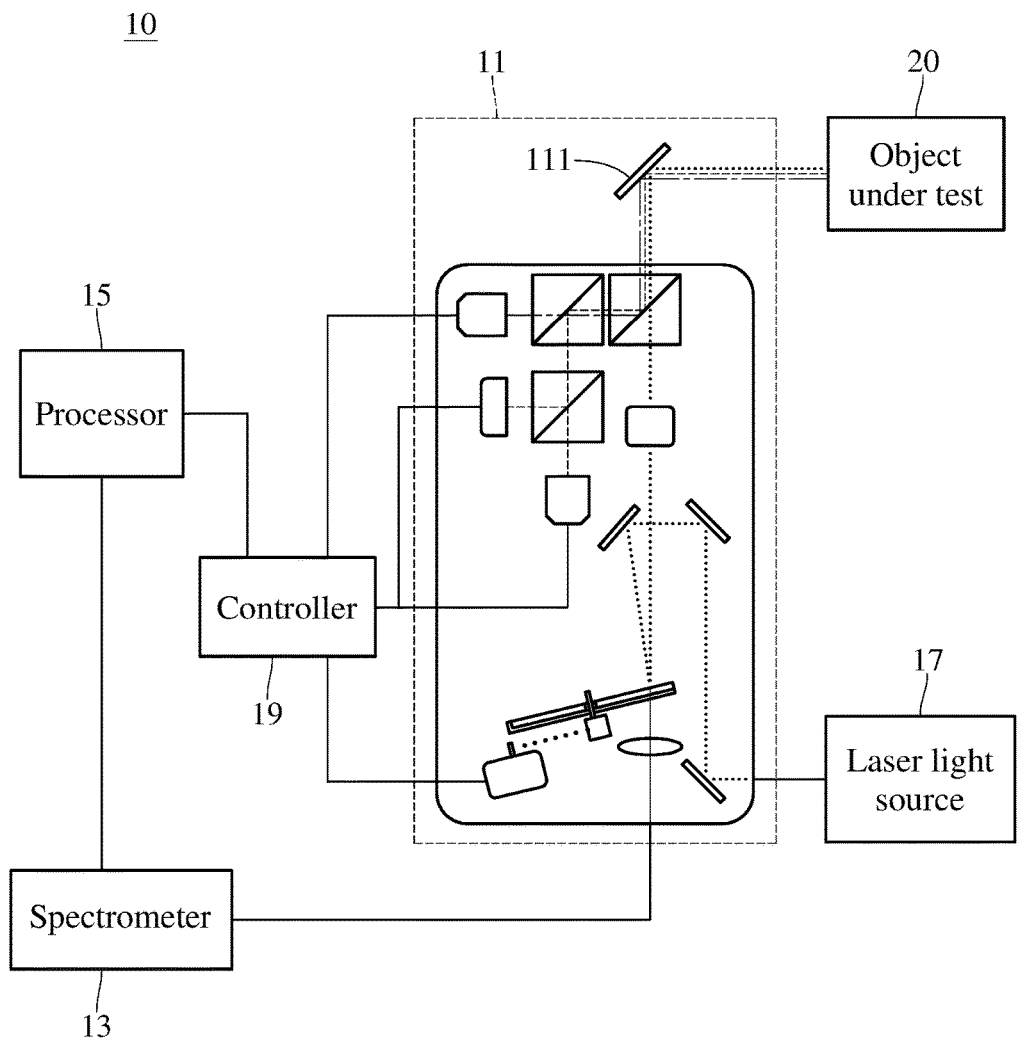
FIG. 1 is a block diagram of a measuring apparatus in an embodiment.

FIG. 1 is a block diagram of a measuring apparatus in an embodiment. A carrier concentration measuring apparatus 10 includes a focuser 11, a spectrometer 13, and a processor 15. The focuser 11 is, for example, a confocal fast autofocus system. The input end of the focuser 11 receives laser beams provided by a laser light source 17 and projects the received laser beam to the object 20. After the object 20 reflects the laser beam propagating from the focuser 11, the focuser 11 receives a radiation, propagating from the object 20, to obtain a Raman signal and then outputs the Raman signal to the spectrometer 13 through its output end.

In practice, the laser light source 17 provides laser beams to the focuser 11 through a fiber cable, and the focuser 11 also sends the obtained Raman signal to the spectrometer 13 through a fiber cable. In au embodiment, the laser beam is, for example, laser light having a high intensity, monochromaticity and directionality. When laser light is projected onto the object 20, the projected laser light will be elastically scattered (i.e. Rayleigh scattering) by elements of the object 20 and be scattered by excitations (i.e. Raman Scattering) because of the Raman Effect. In other words, the Raman signal is, for example, not limited to Rayleigh scattered light, Raman scattered light, or a combination thereof.

When the spectrometer 13 receives the radiation, propagating from the object 20, to obtain a Raman signal, the spectrometer 13 then analyzes the Raman signal to obtain a Raman shift intensity distribution of the Raman signal and set the Raman shift intensity distribution to be the measurement result of the object 20. The spectrometer 13 is electrically connected to the processor 15 so that the spectrometer 13 can transmit the measurement result of the object 20 to the processor 15. Then, the processor 15 determines or analyzes the measurement result of the object 20 to obtain an intensity ratio or a Raman shift, and looks up the carrier concentration of the object 20 in the content stored in a database according to the intensity ratio or the Raman shift.

In an embodiment, the carrier concentration measuring apparatus 10 further includes a controller 19. The controller 19 is electrically connected to the focuser 11 and controls the focuser 11 to project a laser beam having a modulated wavelength onto different positions on the object 20 in order to measure a section to be measured in a depth range of the object 20. A laser beam having a relatively long wavelength can penetrate into the relatively deep part of the object 20. For example, when the object 20 is a wafer implanted with Boron carriers and not annealed, a laser beam of 405 nm wavelength may penetrate into the about 125 nm depth of the object 20 and a laser beam of 325 nm wavelength may penetrate into the about 17 nm depth of the object 20. In another example, when the object 20 is a wafer implanted with phosphorous carriers and annealed, a laser beam of 405 nm wavelength may penetrate into a 120 nm depth of the object 20 and a laser beam of a 325 am wavelength may penetrate into a about 20 nm depth of the object 20.

Such a carrier concentration measurement can be applied to an object, such as wafers implanted with carriers, wafers implanted with carriers and annealed, or other available objects. Note that a wafer implanted with carriers and not annealed has a measurement result different from a measurement result of a wafer implanted with carriers and annealed. These instances of the above wafers are exemplarily described below.

Figure 2A:
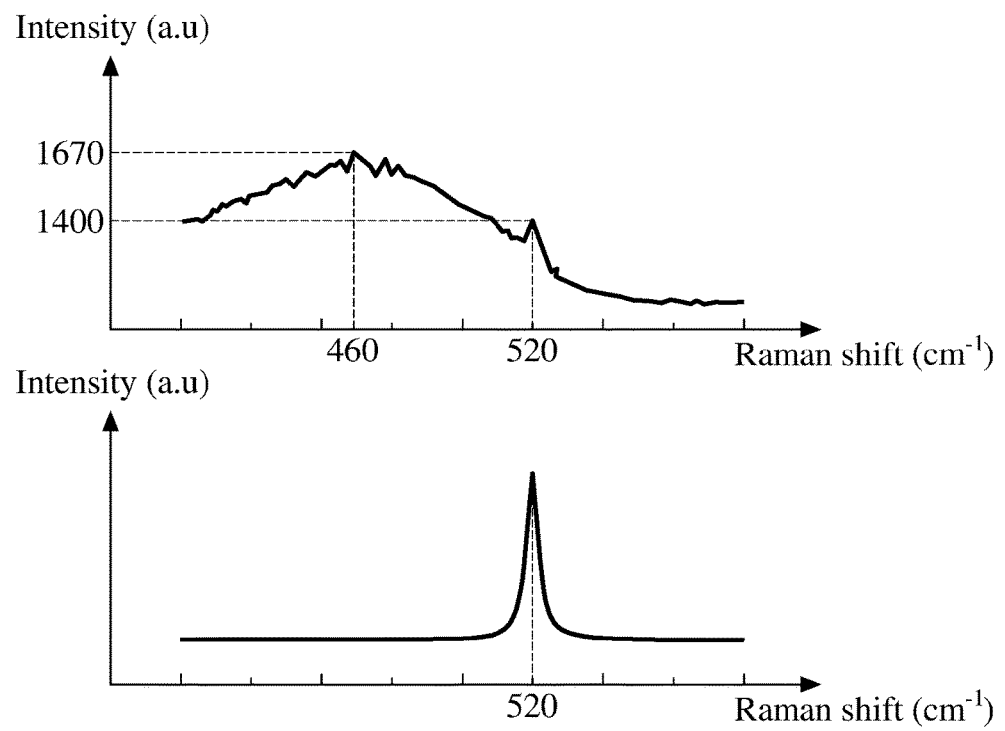
FIG. 2A is a schematic diagram of a relationship between intensities and Raman shifts in an embodiment.

The following description is involved with the object 20 is a silicon wafer implanted with boron carriers and not annealed, and the relationships between intensities and Raman shifts in an embodiment is shown in FIG. 2A. The upper part in FIG. 2A describes a measurement result obtained, when a laser beam having a 405 nm wavelength is used to measure the object 20 and penetrates into about a 125 nm depth of the object 20. The lower part in FIG. 2A describes a measurement result obtained when a laser beam having a 532 nm wavelength is used to measure the object 20 and penetrates into about a 160 nm depth of the object 20.

In the measurement result obtained in the about 125 nm depth, a peak, a first signal point, corresponds to a Raman shift of about 460 Cm$^{-1}$ and an intensity of about 1670 a.u (arbitrary unit), and another peak, a second signal point, corresponds to a Raman shift of about 520 cm$^{-1}$ and an intensity of about 1400 a.u. Then, a ratio of the 1670 a.u intensity corresponding to the 460 cm$^{-1}$ Raman shift to the 1400 a.u intensity corresponding to the 520 cm$^{-1}$ Raman shift is set to be the above intensity ratio, i.e. 1670/1400=1.19. This 1.19 intensity ratio is used to look up the boron carrier concentration, i.e. 4.14×10$^{17}$ (atom/cm$^3$), in the information stored in the database.

As such, the first signal point is associated with carriers in the object 20, and the second signal point is associated with atoms in the object 20. Specifically, the first signal point is a signal point corresponding to a Raman shift obtained when the boron carriers reflect the laser beam, and the second signal point is a signal point corresponding to a Raman shift obtained when silicon atoms reflect the laser beam. The Raman shift herein is a difference in wavenumber between the Rayleigh scattering spectrum line and the Raman scattering spectrum line. Although the above first signal point is defined to correspond to the 460 cm$^{-1}$ Raman shift and the second signal point is defined to correspond to the 520 cm$^1$ Raman shift in this embodiment, other embodiments may be contemplated in which the first and second signal points are defined at two relatively high points corresponding to a Raman shift close to the 460 cm$^{-1}$ Raman shift and a Raman shift close to the 520 cm$^{-1}$ Raman shift, respectively.

In the measurement result obtained in the about 160 nm depth of the object 20, only one peak corresponding to the about 520 cm$^{-1}$ Raman shift exists in the Raman shift intensity distribution, and the concentration of implanted boron carriers in the about 160 nm depth of the object 20 is quite low because of the mono-crystalline silicon in the about 160 Dm depth of the object 20.

Figure 2B:
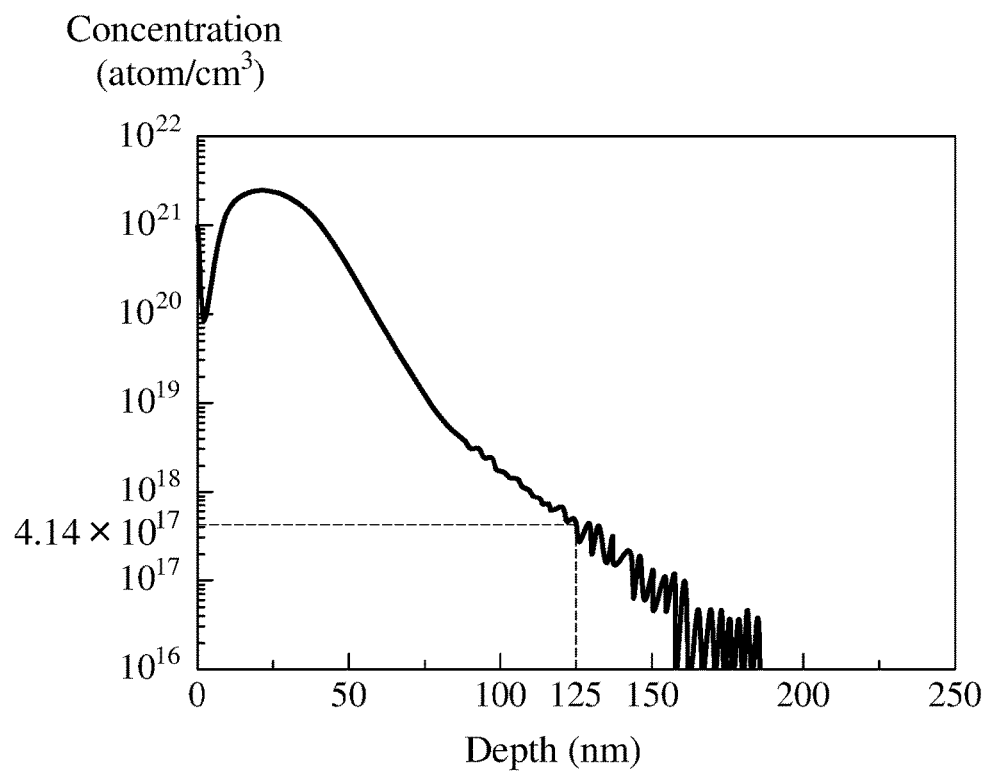
FIG. 2B is a schematic diagram of a relationship between carrier concentrations and depths in an embodiment.
Figure 2C:
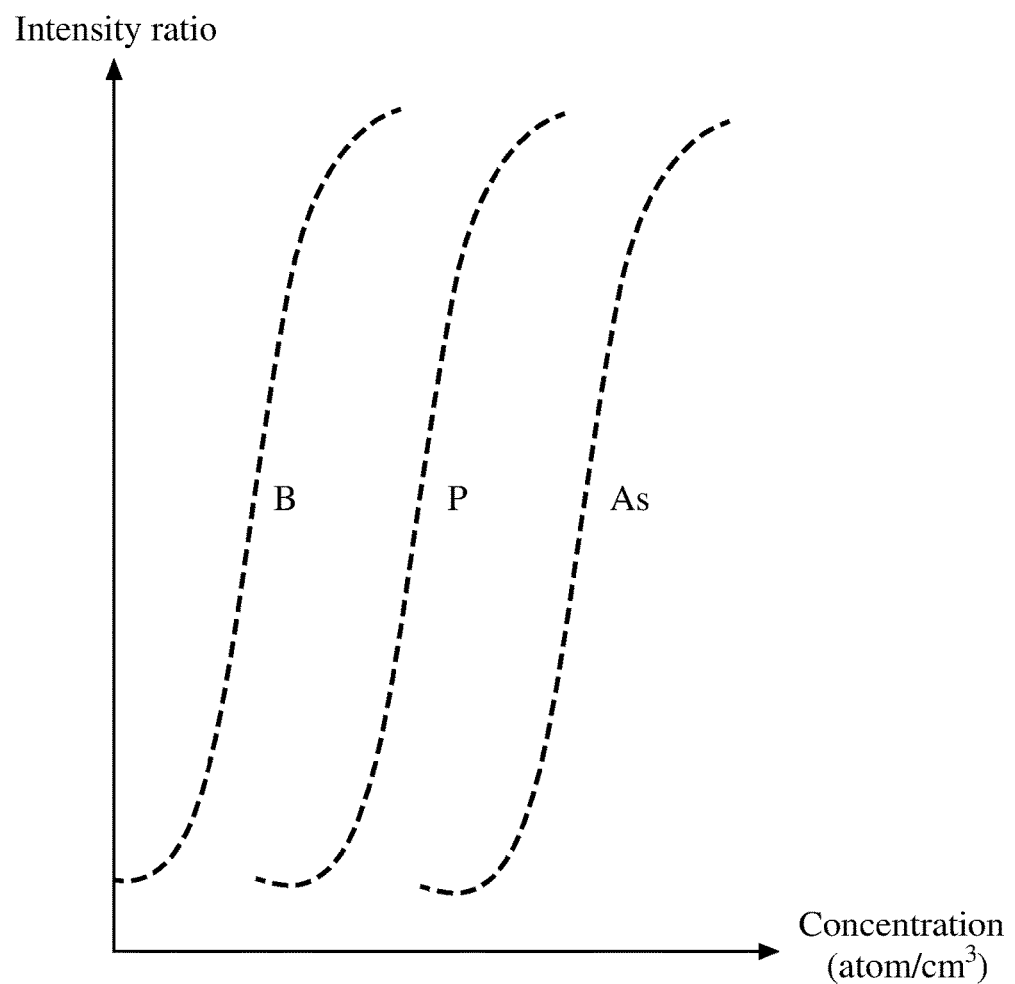
FIG. 2C is a schematic diagram of a relationship between intensity ratios and carrier concentrations in an embodiment.

The following description is involved with how to establish the information stored in the above database with respect to FIG. 2B and FIG. 2C. FIG. 2B is a schematic diagram of a relationship between carrier concentrations and depths in an embodiment, and FIG. 2C is a schematic diagram of a relationship between intensity ratios and carrier concentrations in an embodiment. First, the known information about a relationship between carrier concentrations and depths of a first sample is acquired, and the first sample is a silicon wafer implanted with boron carriers and not annealed.

One of embodiments of acquiring the known information about the relationship between carrier concentrations and depths of a first sample is described as follows. First, use a secondary ion mass spectrometer to analyze the first sample to obtain a carrier concentration distribution about different depths of the first sample. Then, project a laser beam having a different wavelength to the first sample in order to obtain an intensity ratio between a first signal point and a second signal point in a measurement result related to a different depth of the first sample. Finally, link the carrier concentrations in preset depths of the first sample to the intensity ratios obtained using different wavelength laser beams penetrating into the preset depths and store information about a relationship between the carrier concentrations and depths of the first sample into the database.

In this embodiment, for example, when the secondary ion mass spectrometer analyzes the relationship between concentrations and depths of the first sample as shown in FIG. 2B, the carrier concentration in an about 125 nm depth of the first sample is about 4.14×10$^{17}$ (atom/cm$^3$); and when a 405 nm laser beam is projected to the first sample, the intensity ratio corresponding to an about 125 nm depth of the first sample is 1.19. Then, the carrier concentration of 4.14×10$^{17}$ (atom/cm$^3$) measured by the secondary ion mass spectrometer is linked to the intensity ratio of 1.19, whereby a fraction of the information about the relationship between the intensity ratios and concentrations shown in FIG. 2C is established.

Accordingly, after the intensity ratio of 1.19 related to both the first and second signal points is obtained during the analysis of the Raman signal, the known information about the relationship between the intensity ratios and concentrations shown in FIG. 2C can be used to look up the carrier concentration corresponding to the intensity ratio of 1.19, and the carrier concentration corresponding to the intensity ratio of 1.19 is 4.14×10 (atom/cm$^3$).

Figure 3A:
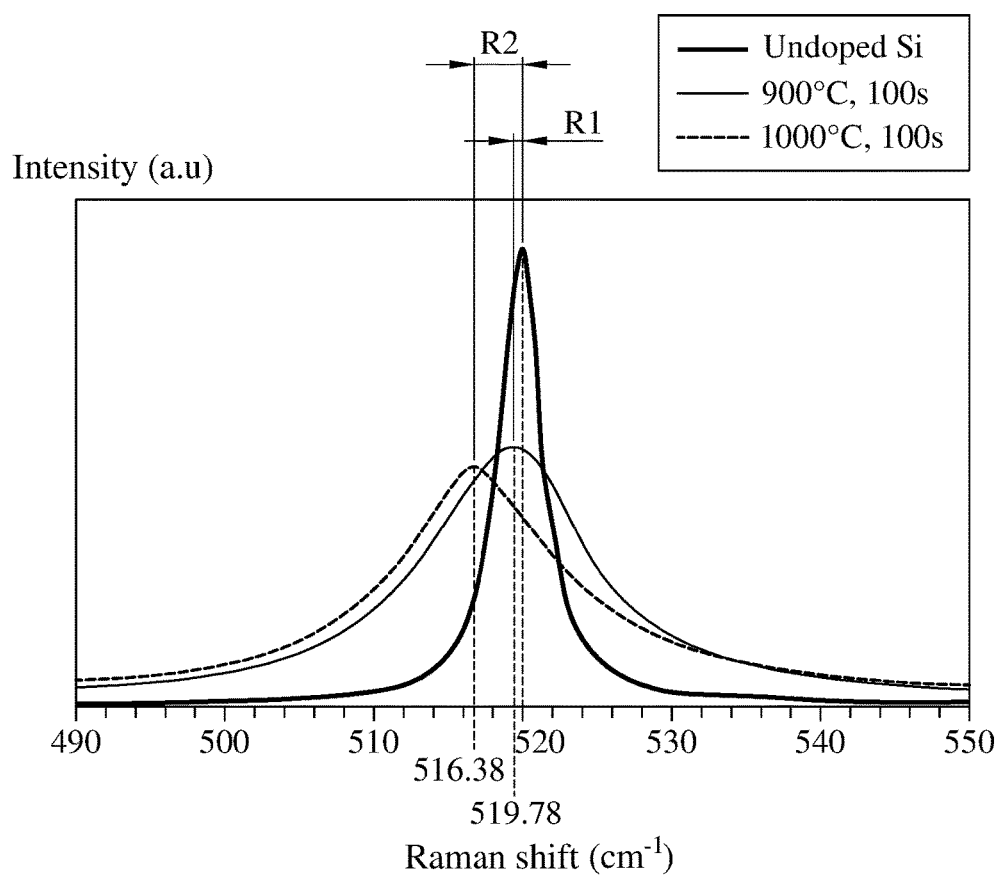
FIG. 3A is a schematic diagram of a relationship between intensities and Raman shifts in another embodiment.

On the other hand, the following description is involved with the measurement result and analysis of the object 20 that is, for example, a silicon wafer implanted with phosphorous carriers and annealed. Please refer to FIG. 1 and FIG. 3A. FIG. 3A is a schematic diagram of a relationship between intensities and Raman shifts in another embodiment. The focuser 11 projects a laser beam having a 405 nm wavelength to the object 20 and the laser beam penetrates into about 120 nm depth of the object 20 in order to measure the carrier concentration in the 120 nm depth of the object 20. The spectrometer 13 analyzes the Raman signal, obtained from the radiation propagating from the object 20, to obtain a measurement result. The processor 15 determines a third signal point in the measurement result and determines a Raman shift corresponding to the third signal point. Then, the processor 15 uses the Raman shift to look up the carrier concentration of the object 20 in the information stored in a database.

In an embodiment, the third signal point is, for example, a signal point having the maximum intensity in the measurement result. In FIG. 3A, the third signal point on a curve related to undoped Si has the maximum intensity and corresponds to a Raman shift of 520 cm$^{-1}$, which is a Raman shift obtained by measuring the mono-crystalline silicon. The third signal point having the maximum intensity on the curve related to 900° C. corresponds to a Raman shift of 519.78 cm$^{-1}$. The third signal point having the maximum intensity on the curve related to 1000□ corresponds to a Raman shift of 516.38 cm$^{-1}$. The temperatures 900□ and 1000□ are temperature settings during annealing.

Then, look up a phosphorous carrier concentration, corresponding to the 519.78 cm$^{-1}$ Raman shift, in the information stored in the database, and look up a phosphorous carrier concentration, corresponding to the 516.38 cm$^{-1}$ Raman shift, in the information stored in the database. The phosphorous carrier concentration corresponding to the 519.78 cm$^{-1}$ Raman shift is 4.25×10$^{19}$ (atom/cm$^3$), and the phosphorous carrier concentration corresponding to the 516.38 cm$^{-1}$ Raman shift is 8.82×10$^{19}$ (atom/cm$^3$). Therefore, the concentration of implanted phosphorous carriers in the about 120 nm depth of the silicon wafer annealed by an environment temperature 900° C. is 4.25×10$^{19}$ (atom/cm$^3$), and the concentration of implanted phosphorous carriers in the about 120 nm depth of the silicon wafer annealed by an environment temperature 1000° C. is 8.82×10$^{19}$ (atom/cm$^3$).

Figure 3B:
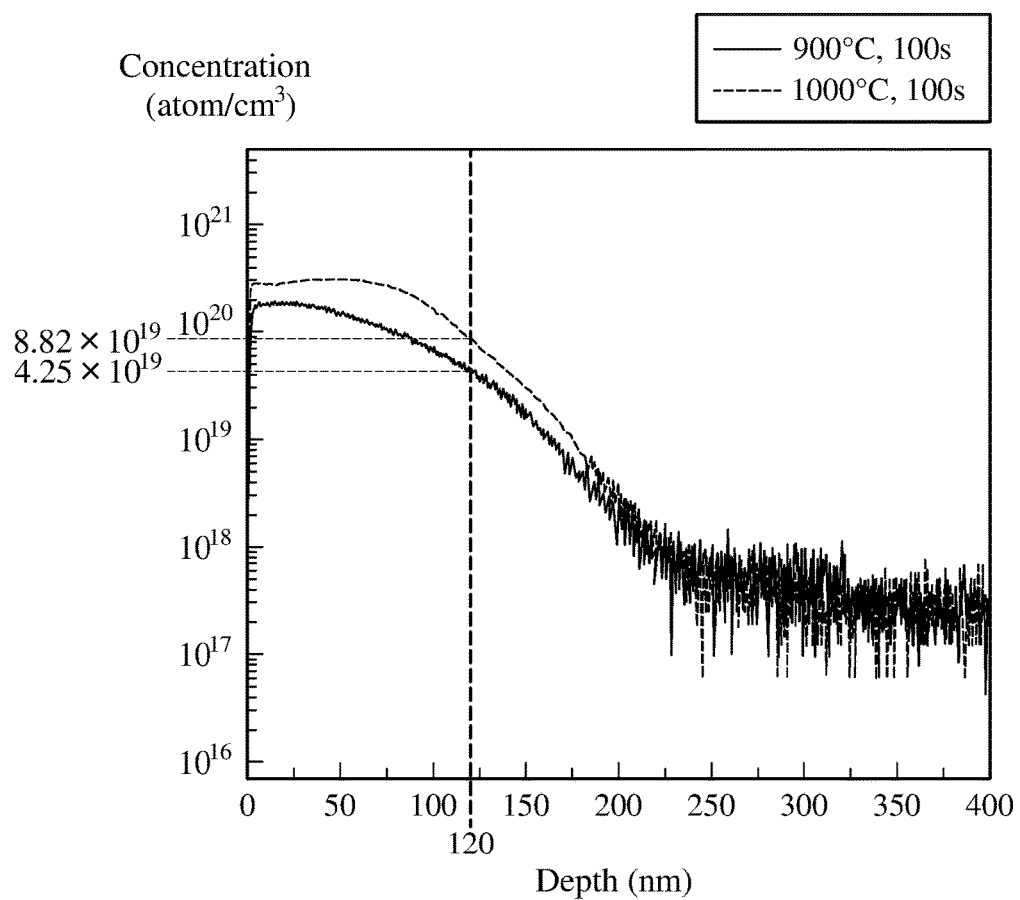
FIG. 3B is a schematic diagram of a relationship between carrier concentrations and depths in another embodiment.
Figure 3C:
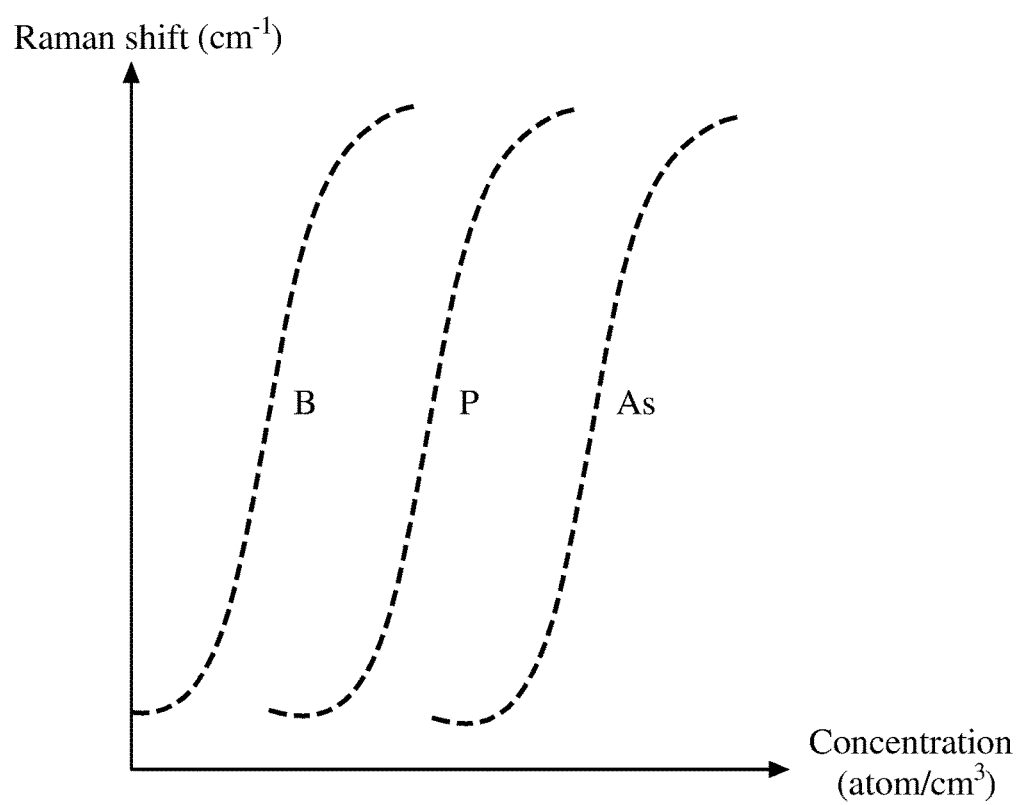
FIG. 3C is a schematic diagram of a relationship between intensity ratios and carrier concentrations in another embodiment.

The following description is involved with how to establish the information stored in the above database with respect to FIG. 3B and FIG. 3C. FIG. 3B is a schematic diagram of a relationship between carrier concentrations and depths in another embodiment, and FIG. 3C is a schematic diagram of a relationship between intensity ratios and carrier concentrations in another embodiment. First, acquire known information about a relationship between carrier concentrations and depths related to a second sample that is, for example, a silicon wafer implanted with phosphorous carriers and annealed. Specifically, a secondary ion mass spectrometer is used to analyze the second sample in order to obtain the information about the relationship between carrier concentrations and depths related to the second sample. Next, a laser beam having a different wavelength is used to measure the second sample in order to obtain a Raman shift corresponding to a third signal point related to a different depth of the second sample. Finally, the carrier concentrations related to different preset depths of the second sample are linked to the Raman shifts related to the different preset depths of the second sample measured by different wavelength laser beams to obtain the relationship between carrier concentrations and depths related to the second sample and store this information in the database.

In the case of the silicon wafer annealed by the environment temperature 1000° C., the known relationship between concentrations and depths related to the silicon wafer is shown in FIG. 3B. The carrier concentration related to the about 120 nm depth of the second sample is 8.82×10$^{19}$ (atom/cm$^3$). When a 405 nm laser beam is used to measure the second sample, the Raman shift related to the about 120 nm depth of the second sample is 516.38 cm$^{-1}$. This carrier concentration of 8.82×10$^{19}$ (atom/cm$^3$) measured by the secondary ion mass spectrometer and this Raman shift of 516.38 cm$^{-1}$ can used to establish, a fraction of the relationship between intensity ratios and carrier concentrations, as shown in FIG. 3C.

In this way, after the Raman shift of 516.38 cm$^{-1}$ corresponding to the third signal point is obtained during the analysis of the measurement result, a carrier concentration corresponding to this Raman shift can be found out in the information about the relationship between intensity ratios and carrier concentrations, as shown in FIG. 3C, and this carrier concentration is 8.82×10$^{19}$ (atom/cm$^3$).

In the aforementioned embodiments, the mentioned values, types of carriers, types of atoms in a wafer, annealing temperatures, Raman shifts, intensities and wavenumbers are exemplary for the illustration purpose rather than for the limitation of the disclosure. Additionally, as described in FIG. 1, in addition to controlling the focuser 11 to modulate the wavelength of the laser beam, the controller 19 also controls a reflection mirror 111 in the focuser 11 to change its rotating angle to project the modulated laser beam to points on the object 20 by the laser scanning projection technology.

Figure 4:
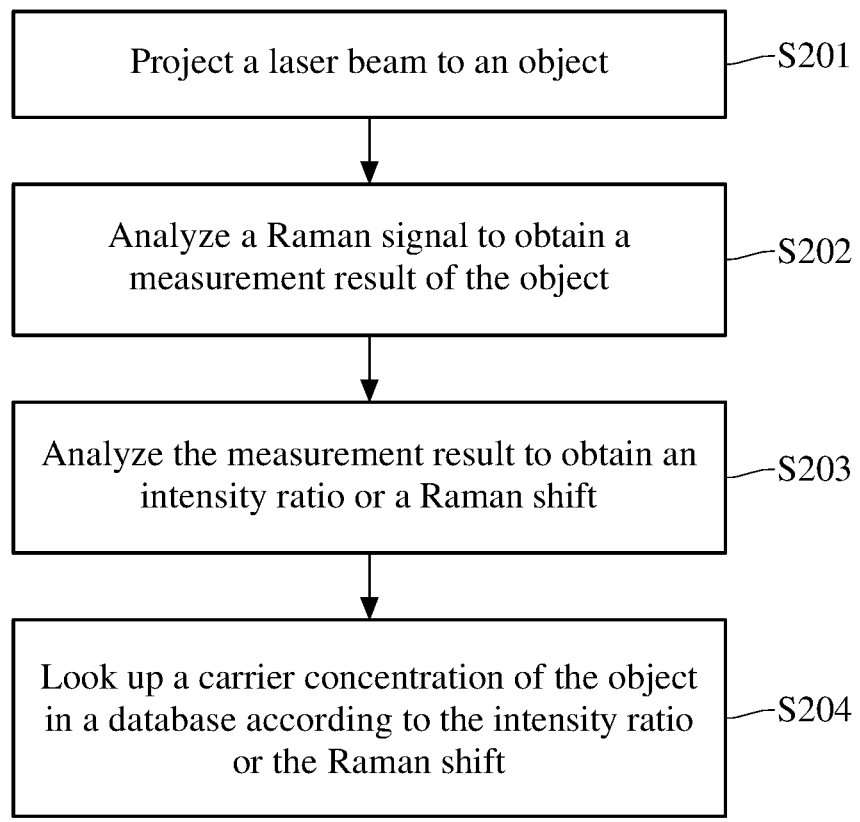
FIG. 4 is a flow chart of a carrier concentration measuring method in an embodiment.

In order to clarify the carrier concentration measuring method, please refer to FIG. 4, which is a flow chart of a carrier concentration measuring method in an embodiment. The carrier concentration measuring method includes the following steps. In step S201, project a laser beam to an object in order to measure it. In step S202, analyze a Raman signal, obtained from a radiation, propagating from the object projected by the laser beam, to obtain a measurement result of the object. In step S203, analyze the measurement result to obtain an intensity ratio or a Raman shift. In step S204, use the intensity ratio or the Raman shift to look up a carrier concentration of the object in the information stored in a database.

As set forth above, the disclosure provides a carrier concentration measuring method and an apparatus thereof to employ a laser beam and the Raman effect to measure an object and obtain a Raman signal, acquired from a radiation propagating from the object projected by the laser beam. Then, the disclosure analyzes the Raman signal to obtain a Raman shift intensity distribution and determines the Raman shift intensity distribution to obtain an intensity ratio or a Raman shift related to the object. Finally, the intensity ratio or the Raman shift is used to look up the carrier concentration of the object in the information stored in a database. Moreover, the disclosure also provides instances of how to establish the database. Accordingly, the disclosure is capable of measuring objects by a non-destructive test method and also can be applied to any carrier concentration measurement workstation in production lines.

What is claimed is:

1. A carrier concentration measuring method, comprising:
projecting a laser beam to an object;
receiving the laser beam reflected by the object to form a first Raman signal;
analyzing the first Raman signal to obtain a first measurement result of the object, wherein the first measurement result comprises a Raman shift intensity distribution, and the Raman shift intensity distribution comprises a first signal point corresponding to a first Raman shift and a second signal point corresponding to a second Raman shift;
determining an intensity of the first signal point and an intensity of the second signal point in the first measurement result;

obtaining an intensity ratio according to a relationship between the intensity of the first signal point and the intensity of the second signal point; and looking up a carrier concentration of the object in a database according to the intensity ratio, wherein the laser beam has a modulated wavelength and is reflected by a section to be measured in a depth range of the object to form the first Raman signal, the object is a wafer that is implanted with carriers, the first signal point is associated with the carriers in the depth range of the object, and the second signal point is associated with atoms in the depth range of the object.

2. The carrier concentration measuring method according to claim 1, further comprising:

analyzing carrier concentrations in different preset depths of a first sample by a secondary ion mass spectrometer, the first sample being implanted with carriers;

projecting the laser beam having a different wavelength to the first sample to obtain the intensity ratio in each of the preset depths of the first sample; and establishing the database storing information about relationships between the carrier concentrations and the intensity ratios in the preset depths of the first sample.

3. The carrier concentration measuring method according to claim 1, further comprising:

annealing the object after obtaining the first Raman signal;

projecting the laser beam to the object which is annealed;

receiving the laser beam reflected by the object, which is annealed, to form a second Raman signal;

analyzing the second Raman signal to obtain a second measurement result of the object which is annealed, wherein the second measurement result comprises a third signal point corresponding to a third Raman shift; and looking up the carrier concentration of the object, which is annealed, in the database according to the third Raman shift.

4. The carrier concentration measuring method according to claim 3, wherein an intensity of the third signal point is stronger than intensities of neighboring signal points in the second measurement result.

5. The carrier concentration measuring method according to claim 4, further comprising:

analyzing carrier concentrations in different preset depths of a second sample by a secondary ion mass spectrometer, and the second sample being implanted with carriers and annealed;

projecting the laser beam of a different wavelength to the second sample to obtain a Raman shift in each of the preset depths of the second sample; and establishing the database storing information about relationships between the carrier concentrations and the Raman shifts in the preset depths of the second sample.

6. The carrier concentration measuring method according to claim 3, wherein both the first Raman signal and the second Raman signal are generated by reflection of the laser beam at the depth range of the object.

7. A carrier concentration measuring apparatus, comprising:

a focuser, configured to project a laser beam to an object and receive the laser beam reflected by the object to form a first Raman signal;

a spectrometer, configured to analyze the first Raman signal to generate a first measurement result of the object, wherein the first measurement result comprises a Raman shift intensity distribution, and the Raman shift intensity distribution comprises a first signal point corresponding to a first Raman shift and a second signal point corresponding to a second Raman shift;

a processor, configured to process the first measurement result to determine an intensity of the first signal point and an intensity of the second signal point, obtain an intensity ratio according to a relationship between the intensity of the first signal point and the intensity of the second signal point, and look up a carrier concentration of the object in a database according to the intensity ratio;

a laser light source configured to provide laser light to the focuser; and a controller configured to control the focuser to generate the laser beam having a modulated wavelength and project the laser beam toward different position on the object in order to measure a section to be measured in a depth range of the object, wherein the object is a wafer implanted with carriers, the first signal point is associated with the carriers in the depth range of the object, and the second signal point is associated with atoms in the depth range of the object.

8. The carrier concentration measuring apparatus according to claim 7, wherein the object is annealed after obtaining the first Raman signal, the focuser is further configured to project the laser beam to the object which is annealed and receive the laser beam reflected by the object to form a second Raman signal, the spectrometer is further configured to analyze the second Raman signal to generate a second measurement result of the object which is annealed, the processor determines a third signal point in the second measurement result and obtains a third Raman shift according to the third signal point.

9. The carrier concentration measuring apparatus according to claim 8, wherein an intensity of the third signal point is stronger than intensities of neighboring signal points in the second measurement result.

10. The carrier concentration measuring apparatus according to claim 8, wherein both the first Raman signal and the second Raman signal are generated by reflection of the laser beam at the depth range of the object.

* * * * *